United States Patent
Hale et al.

(10) Patent No.: US 6,689,068 B2
(45) Date of Patent: Feb. 10, 2004

(54) AUTOMATIC PRESSURE RANGE AND SENSITIVITY ADJUSTMENT

(75) Inventors: Curtis A. Hale, Chisago City, MN (US); Kathleen A. Prieve, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 201 days.

(21) Appl. No.: 10/033,815

(22) Filed: Dec. 20, 2001

(65) Prior Publication Data

US 2003/0120161 A1 Jun. 26, 2003

(51) Int. Cl.[7] .............................................. A61B 05/00
(52) U.S. Cl. ....................... 600/485; 600/486; 600/488; 600/490; 600/561; 73/760
(58) Field of Search ................................. 600/485, 486, 600/488, 490, 493–496, 500–503, 561; 73/760–860

(56) References Cited

U.S. PATENT DOCUMENTS

| | | | |
|---|---|---|---|
| 4,080,653 A | * 3/1978 | Barnes et al. ............... | 600/561 |
| 5,535,752 A | 7/1996 | Halperin et al. | |
| 5,564,434 A | * 10/1996 | Halperin et al. ............ | 600/488 |
| 6,245,022 B1 | * 6/2001 | Archibald et al. .......... | 600/485 |
| 6,248,080 B1 | * 6/2001 | Miesel et al. ............... | 600/561 |

* cited by examiner

Primary Examiner—Robert L. Nasser
(74) Attorney, Agent, or Firm—Girma Wolde-Michael; Michael C. Soldner (57) ABSTRACT

The invention automatically adjusts the parameters that map pressures at a monitoring site, such as blood pressures in the chamber of a heart, to digital values. Adjusting the mapping parameters keeps the data in range while preserving sensitivity. A histogram of the digital pressure data is generated and the contents of the lowest and highest bins of the histogram are checked. Depending on whether the boundary bins of the histogram are full or empty, the mapping parameters are adjusted. A new histogram is generated using digital values generated with the adjusted mapping parameters.

38 Claims, 5 Drawing Sheets

AUTOMATIC PRESSURE RANGE AND SENSITIVITY ADJUSTMENT

TECHNICAL FIELD

The invention relates to medical monitoring, and in particular, to pressure sensing by an implanted medical device.

BACKGROUND

There are many situations in which a patient requires long-term monitoring and when it may be desirable to implant a sensor for monitoring within the body of the patient. One such monitor is a pressure monitor, which can measure the pressure at a site in the body, such as a blood vessel or a chamber of the heart. When implanted in a vessel or a heart chamber, the sensor responds to changes in blood pressure at that site. Blood pressure is measured most conveniently in units of millimeters of mercury (mm Hg) (1 mm Hg=133 Pa).

The implanted pressure sensor is coupled to an implanted medical device, which receives analog signals from the sensor and processes the signals. Signals from the implanted pressure sensor may be affected by the ambient pressure surrounding the patient. If the patient is riding in an airplane or riding in an elevator in a tall building, for example, the ambient pressure around the patient may change. Changes in the ambient pressure affect the implanted pressure sensor, and may therefore affect the signals from the pressure sensor.

A typical implanted device that employs a pressure sensor is not concerned with total pressure, i.e., blood pressure plus ambient pressure. Rather, the device typically is designed to monitor blood pressure at the site of the internal sensor. To provide some compensation for changes in ambient pressure, some medical devices take additional pressure measurements with an external pressure sensor. The external pressure sensor, which may be mounted outside the patient's body, responds to changes in ambient pressure, but not to changes in blood pressure. The blood pressure is a function of the difference between the signals from the internal and external pressure sensors.

Although the internal pressure sensor may generate analog pressure signals as a function of the pressure at the monitoring site, the pressure signals are typically converted to digital signals, i.e., a set of discrete binary values, for digital processing. An analog-to-digital (A/D) converter receives an analog signal, samples the analog signal, and converts each sample to a discrete binary value. In other words, the pressure sensor generates a pressure signal as a function of the pressure at the monitoring site, and the A/D converter maps the pressure signal to a binary value.

The A/D converter can generate a finite number of binary values. An 8-bit A/D converter, for example, can generate 256 discrete binary values. The maximum binary value corresponds to a maximum pressure signal, which in turn corresponds to a maximum pressure at the monitoring site. Similarly, the minimum binary value corresponds to a minimum pressure signal, which in turn corresponds to a minimum site pressure. Accordingly, there is a range of pressure signals, and therefore a range of site pressures, that can be accurately mapped to the binary values.

In a patient, the actual site pressures are not constrained to remain between the maximum and minimum monitoring site pressures. Due to ambient pressure changes or physiological factors, the pressure sensor may experience a site pressure that is "out of range," i.e., greater than the maximum monitoring site pressure or less than the minimum monitoring site pressure. In response to an out-of-range pressure, the pressure sensor generates an analog signal that is greater than the maximum pressure signal or less than the minimum pressure signal. An out-of-range pressure cannot be mapped accurately to a binary value.

For example, the pressure sensor may experience a high pressure at the monitoring site that exceeds the maximum site pressure. In response, the pressure signal generates a pressure signal that exceeds the maximum pressure signal. The pressure signal is sampled and the data samples are supplied to the A/D converter. When the A/D converter receives a data sample that is greater than the maximum pressure signal, the A/D converter maps the data sample to a binary value that reflects the maximum pressure signal, rather than the true value of the data sample. In other words, the data sample is "clipped" to the maximum binary value. Similarly, when the A/D converter receives a data sample that is below the minimum pressure signal, the converter generates a binary value that reflects the minimum pressure signal rather than the true value of the data sample.

Because of changes in ambient pressure, pressures sensed by the internal pressure sensor may be in range at one time and move out of range at another time. When the pressures move out of range, some data associated with the measured pressures may be clipped, and some data reflecting the true site pressures may be lost. In such a case, the binary values may not accurately reflect the true blood pressures at the monitoring site.

To avoid clipping, the implanted device may be programmed to accommodate an expected range of site pressures. Estimating the expected range of site pressures is difficult, however, because ambient pressure may depend upon factors such as the weather, the patient's altitude and the patient's travel habits. Pressures may be in range when the patient is in one environment, and out of range when the patient is in another environment.

The risk of clipping can further be reduced by programming the implanted device with a high maximum site pressure that corresponds to the maximum binary value and with a low minimum site pressure that corresponds to the minimum binary value. Programming the device for a high maximum and a low minimum creates a safety margin. The price of safety margins, however, is a loss of sensitivity. Safety margins mean that pressures near the maximum and minimum site pressures are less likely to be encountered. As a result, many of the largest and smallest binary values are less likely to be used, and the digital data is a less precise representation of the site pressures.

SUMMARY

In general, the invention is directed to a pressure monitor for use in an implantable medical device that uses automatic pressure range adjustment to keep data samples within the range of an A/D converter, and thereby avoid clipping. In addition, the invention automatically adjusts pressure range to preserve high sensitivity.

An A/D converter maps signals from a pressure sensor to binary values, which are supplied to a controller such as a microprocessor. The controller generates a histogram of the digital pressure data from the binary values. The histogram reflects the distribution of the digital pressure data, which in turn should reflect the distribution of pressures at the monitoring site. The histogram is divided into a number of "bins"

that correspond to a set of pressure values. The contents of the bins are a function of the pressures at the monitoring site. The contents of the bins are also a function of the parameters that define how site pressures are mapped to binary values. The distribution of digital pressure data in the bins therefore not only provides useful information about the pressures at the monitoring site, but also information as to whether there is a risk of data going out of range. The distribution of pressure values in the bins further provides information as to whether there is "unused range," i.e., a range of binary values that was not used.

The controller senses the possibility of out-of-range data or unused range by sensing the contents of the lowest and highest bins of the histogram. If the lowest bin is full, for example, that may indicate that data are out of range on the low side. If there are several bins on the low side that are empty, however, that may indicate that range on the low side is not being efficiently utilized. Similar conditions are checked on the high end of the histogram. When it appears that data may be out of range or that range is not being used, the controller adjusts the mapping parameters, with the goal of generating a new histogram that does not have the same problems.

One way in which the controller may adjust the histogram parameters is by controlling the gain and the offset of an amplifier. Adjusting the gain expands or decreases the range of pressure signals that are supplied to the A/D converter. Adjusting the offset moves the range of pressure signals up or down.

In one embodiment, the invention is directed to a method comprising mapping a set of blood pressures to a set of discrete binary values with first mapping parameters. The first mapping parameters include a maximum binary value that corresponds to a maximum blood pressure and a minimum binary value that corresponds to a minimum blood pressure. The method also includes generating a histogram with the set of discrete binary values and generating second mapping parameters as a function of the contents of the lowest bin and the highest bin of the histogram. The second mapping parameters may be generated by adjusting the gain and/or offset of an amplifier. The method may further include mapping a second set of blood pressures to a second set of discrete binary values with the second mapping parameters and generating a second histogram with the second set of discrete binary values.

In another embodiment, the invention is directed to a computer-readable medium containing instructions that cause a programmable processor to carry out this method.

In further embodiment, the invention is directed to a device comprising an amplifier, an analog-to-digital converter and a controller. The amplifier generates pressure signals as a function of pressure sensed by a pressure sensor in a body and as a function of mapping parameters, and the analog-to-digital converter that converts the pressure signals to a set of discrete binary values. The controller generates a first histogram as a function of a distribution of a first set of binary values. The controller also generates second mapping parameters as a function of the distribution of data in the first histogram.

In an additional embodiment, the invention presents a method comprising receiving analog pressure data, mapping the analog pressure data to discrete binary values with first mapping parameters, generating a first histogram as a function of the distribution of the discrete binary values during a storage interval and, after the storage interval, generating second mapping parameters as a function of the contents of the lowest bin and the highest bin of the histogram.

The invention can provide a number of advantages. For example, the invention automatically reduces the risk that data may go out of range and be clipped, by automatically adjusting the range of the data, thereby automatically correcting for changes in the ambient air pressure experienced by the patient. The patient's physician need not program the device with an expected maximum and minimum pressure values. In addition, the invention automatically keeps the data in range with little adverse effect on sensitivity. The invention also increases sensitivity when unused range is detected.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
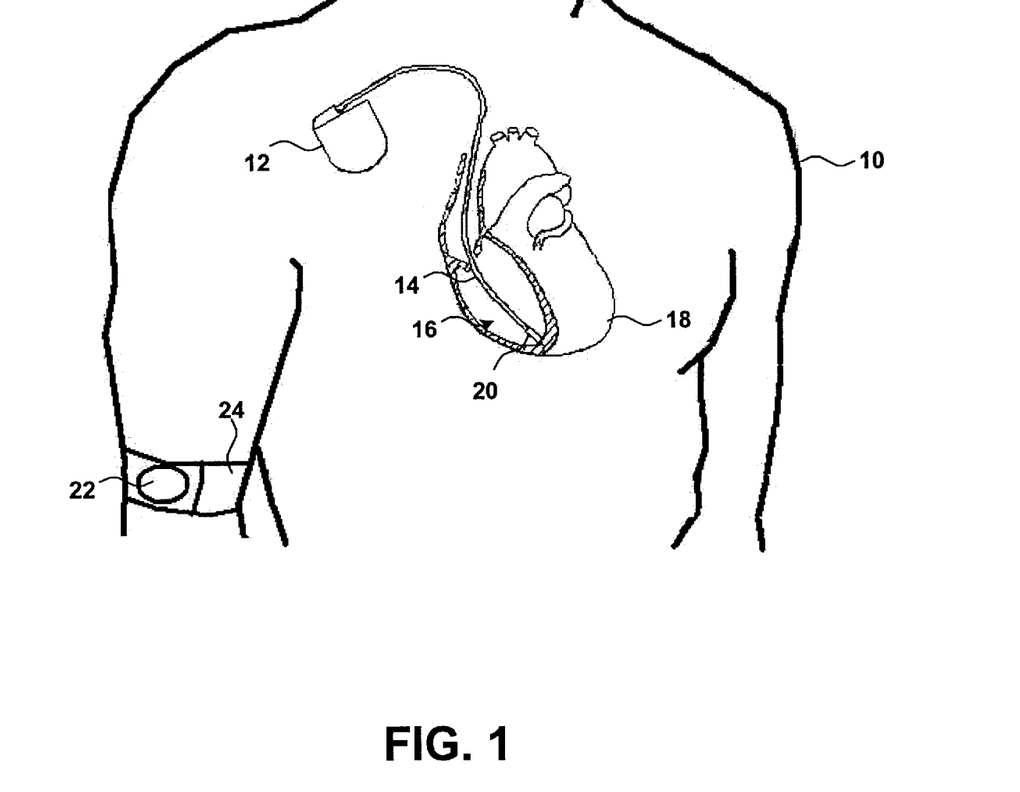
FIG. 1 is a diagram of a human body with an implanted medical device and pressure sensors.

FIG. 1 is a diagram of a body of a patient 10 having an implanted medical device 12. Coupled to implanted medical device 12 is a lead 14 that extends into the right ventricle 16 of the heart 18. An implanted pressure sensor 20 disposed in right ventricle 16 is coupled to lead 14 and responds to changes in blood pressure in right ventricle 16. The blood pressure in right ventricle 16 is a function of factors such as the volume of right ventricle 16, the pressure exerted by the contraction of heart 18 and the ambient pressure around patient 10.

Implanted medical device 12 receives analog signals from implanted pressure sensor 20 via lead 14. The signals are a function of the pressure sensed by implanted pressure sensor 20 at the monitoring site, i.e., right ventricle 16.

Patient 10 carries an external pressure sensor 22. FIG. 1 shows external pressure sensor 22 coupled to a belt 24 on the arm of patient 10, but this is one of many possible sites for external pressure sensor 22. External pressure sensor 22 responds to changes in ambient pressure, and is unaffected by blood pressure in right ventricle 16. Implanted medical device 12 may receive signals from external pressure sensor 22 via communication such as radio frequency telemetry. Alternatively, implanted medical device 12 need not communicate with external pressure sensor 22 in any way.

Implanted medical device 12 includes a digital processor. The analog signals from implanted pressure sensor 20 are converted to digital signals for processing. The analog signals are amplified by an amplifier 32 (shown in FIG. 2) and are sampled and are mapped to discrete binary values by an A/D converter 34 (shown in FIG. 2). Each binary value corresponds to a pressure signal that in turn corresponds to a site pressure. A/D converter 34 maps each sample to a binary value that corresponds most closely to the actual pressure signal and site pressure reflected by the sample.

The sensitivity of implanted medical device 12 to changes in pressure is a function of the range of pressures that map to a single binary value. The smaller the pressure change represented by consecutive binary values, the more sensitive implanted medical device 12 is to changes in pressure. For example, an 8-bit A/D converter may be configured to map pressures between a minimum site pressure of 760 mm Hg and a maximum site pressure of 860 mm Hg to discrete binary values. In this example, a one-bit increase represents a pressure increase of about 0.4 mm Hg.

In a conventional implanted medical device, there may be a tradeoff between range and sensitivity. When the number of possible discrete binary values is fixed, expanding the range of site pressures that are represented by the binary values results in a decrease in sensitivity, because a one-bit change represents a larger pressure change. Similarly, decreasing the range results in an increase in sensitivity because a one-bit change represents a smaller pressure change.

In an illustrative example, an 8-bit A/D converter may be configured to map pressures between 760 mm Hg and 860 mm Hg to discrete binary values, with a one-bit increase representing a pressure increase of about 0.4 mm Hg. When the same 8-bit A/D converter is configured to map pressures between 746 mm Hg and 874 mm Hg to discrete binary values, the overall range of site pressures that can be mapped to binary values expands by 28 mm Hg. The sensitivity, however, decreases. A one-bit increase represents a pressure increase of 0.5 mm Hg.

Not all changes to range affect sensitivity. In some circumstances, a range may be offset without affecting sensitivity. In an offset, the minimum site pressure and the maximum site pressure are increased or decreased by the same amount. For example, a 8-bit A/D converter may be configured to map pressures between 760 mm Hg and 860 mm Hg to discrete binary values, with a one-bit increase representing a pressure increase of about 0.4 mm Hg. When the pressure range is shifted downward to pressures between 740 mm Hg and 840 mm Hg, the range is offset but not expanded. When the range is offset, sensitivity is not affected. A one-bit increase still represents a pressure increase of about 0.4 mm Hg.

Implanted medical device 12 implements techniques for automatically adjusting mapping parameters in response to changes in pressure conditions. In particular, implanted medical device 12 periodically evaluates the digital pressure data to determine whether pressure data may be going out of range, and expands and/or offsets the range to avoid having data go out of range. In addition, implanted medical device 12 determines whether the range can be decreased so that sensitivity can be enhanced.

Figure 2:
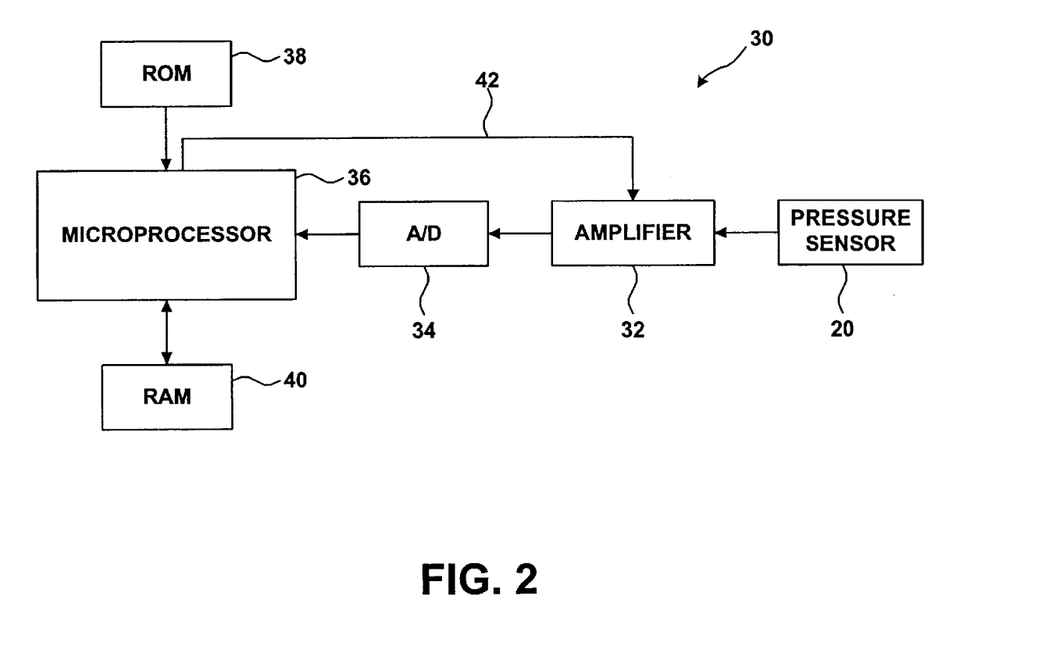
FIG. 2 is a block diagram illustrating an exemplary system that implements the invention.

FIG. 2 is a block diagram of an exemplary system 30 that implements the invention. Pressure sensor 20 supplies an analog pressure signal to amplifier 32. The analog pressure signal is a function of the site pressure, where pressure sensor 20 is disposed. The analog pressure signal may be, for example, a voltage signal. Amplifier 32 amplifies the signal by, for example, amplifying the voltage. Amplifier 32 may perform other operations such as serving as an anti-aliasing filter. Amplifier 32 has an adjustable gain and an adjustable offset. The gain and offset of amplifier 32 are adjustable under the control 42 of a controller, which may take the form of a microprocessor 36. The controller may take other forms, such as an application-specific integrated circuit (ASIC), a field programmable gate array (FPGA), or any other circuit including discrete and/or integrated components and that has control capabilities.

Amplifier 32 supplies the amplified analog signal to A/D converter 34. The range of pressure signals supplied to A/D converter 34 is a function of the gain of amplifier 32 and the offset of amplifier 32. By adjusting the gain and/or offset of amplifier 32, microprocessor 36 regulates the mapping parameters, i.e., the correspondence between site pressures and binary values. A/D converter 34 samples the pressure signals from amplifier 32 and converts the samples into discrete binary values, which are supplied to microprocessor 36. In this way, microprocessor 36, amplifier 32 and A/D converter 34 cooperate to map the site pressures to binary values.

The number of possible discrete binary values that can be generated by A/D converter 34 is fixed. When there is a risk of data out of range, it is not feasible to increase the number of binary values that represent the site pressures. As will be described in more detail below, microprocessor 36 adjusts the gain and/or the offset of amplifier 32 so that the data remain in range and so that the digital pressure data generated by A/D converter 34 accurately reflect the site pressures sensed with pressure sensor 20.

Microprocessor 36 processes the digital pressure data according to algorithms embodied as instructions stored in memory units such as read-only memory (ROM) 38 or random access memory (RAM) 40. Microprocessor 36 may, for example, control a therapy delivery system (not shown in FIG. 2) as a function of the digital pressure data.

Microprocessor 36 may further compile statistical information pertaining to the digital pressure data. In one embodiment, microprocessor 36 generates a histogram of the digital pressure data. The histogram, which may be stored in RAM 40, reflects the distribution of pressures sensed by pressure sensor 20.

The histogram includes a plurality of "bins," i.e., a plurality of numbers of digital data samples of comparable magnitude. For example, a histogram that stores the number of digital values corresponding to pressures between 760 mm Hg and 860 mm Hg may include twenty bins, with each bin recording the number of data samples that fall in a 5 mm Hg span. The first bin holds the number of values between 760 mm Hg and 765 mm Hg, while the second bin holds the number of values between 765 mm Hg and 770 mm Hg, and so on. More or fewer bins may be used.

The distribution of values in the bins provides useful information about the pressures in right ventricle 16. Data accumulates in the histogram over a period of time called a "storage interval," which may last a few seconds, a few hours or a few days. At the end of the storage interval, microprocessor 36 stores in RAM 40 information about the distribution of pressures, such as the mean, the standard deviation, or pressure values at selected percentiles. Microprocessor 36 may then clear data from the histogram and begin generating a new histogram.

When microprocessor 36 adjusts the mapping parameters, the new histogram may be different from the preceding histogram. In particular, the new histogram may record the distribution of an expanded range of pressure data, or a reduced range of pressure data, or a range that has been offset up or down. In general, the adjustments to the mapping parameters tend to center the distribution in the histogram, and tends to reduce the number of values in the highest and lowest bins. Microprocessor 36 adjusts the mapping parameters based upon the distribution of digital pressure data in the preceding histogram. Microprocessor 36 may make the adjustments to avoid data out of range, to avoid having unused range, or both.

In one embodiment of the invention, microprocessor 36 senses the possibility of out-of-range data or unused range by sensing the contents of the boundary bins of the histogram, i.e., by checking whether the data distribution has assigned values to the bins that accumulate the lowest values and the highest values of the histogram. As a result of checking the bins, microprocessor 36 may automatically adjust the gain, or the offset, or both of amplifier 32.

Figure 3:
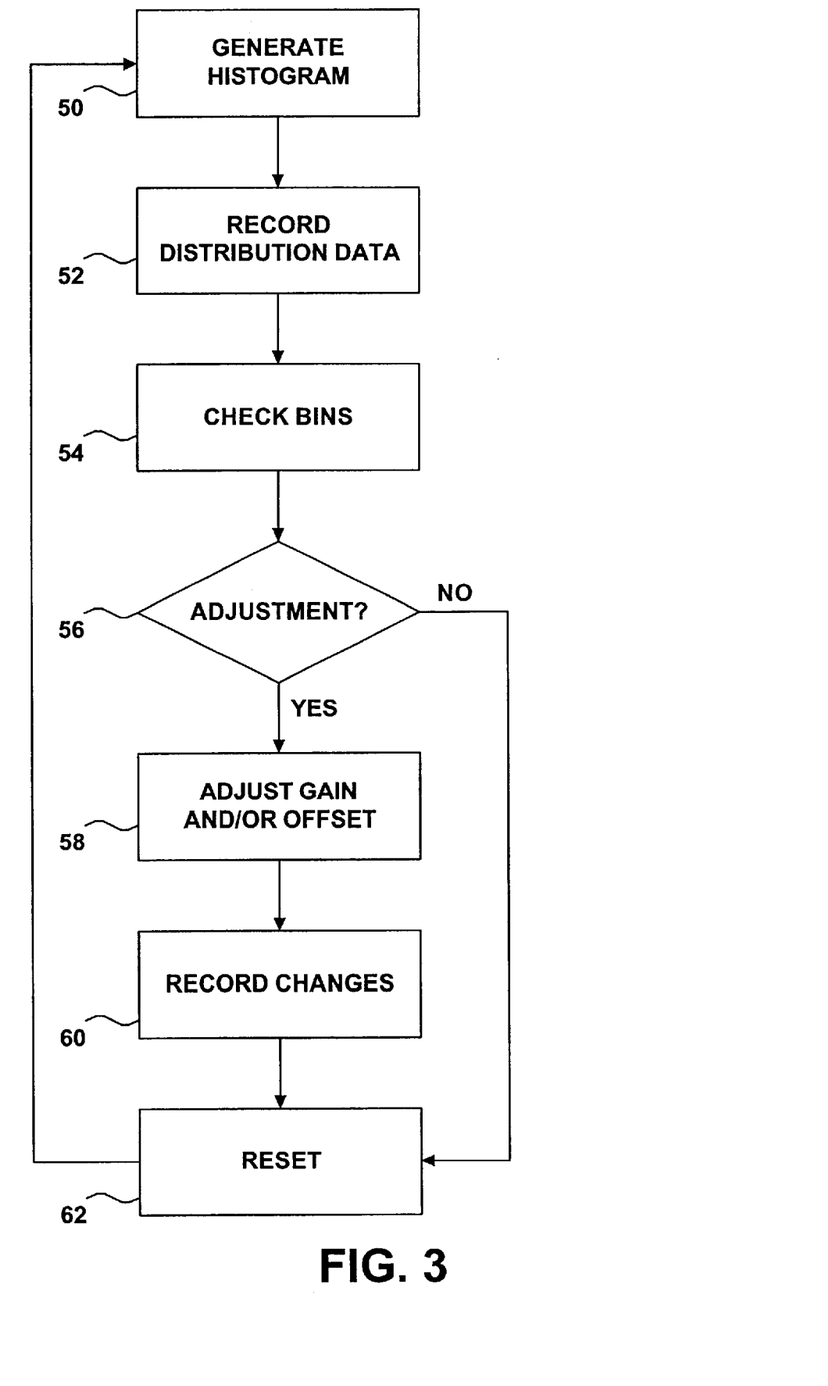
FIG. 3 is a flow diagram illustrating adjustment to mapping parameters, based upon the distribution in a histogram generated earlier.

FIG. 3 is a flow diagram illustrating techniques for automatically adjusting the gain, or the offset, or both, in response to the distribution of values in a histogram. Microprocessor 36 generates the histogram (50), reflecting the distribution digital pressure data, which in turn reflects site pressures sensed by pressure sensor 20 over a storage interval. The digital pressure data are related to the site pressures by a set of mapping parameters.

The histogram includes a plurality of bins. Generating the histogram causes data to accumulate in the bins. When the storage interval ends and the data have accumulated in the histogram, microprocessor 36 may periodically store information about the distribution of the data (52), such as the mean, the standard deviation, or values at particular percentiles.

Before beginning a new storage interval, microprocessor 36 determines whether there is a risk of data being out of range or whether there is unused range. Depending on this determination, an adjustment to the mapping parameters may be made. Microprocessor 36 checks the highest and lowest bins of the histogram (54) and makes a decision as to whether to adjust the mapping parameters (56) as a function of the contents of the highest and lowest bins.

Figure 4:
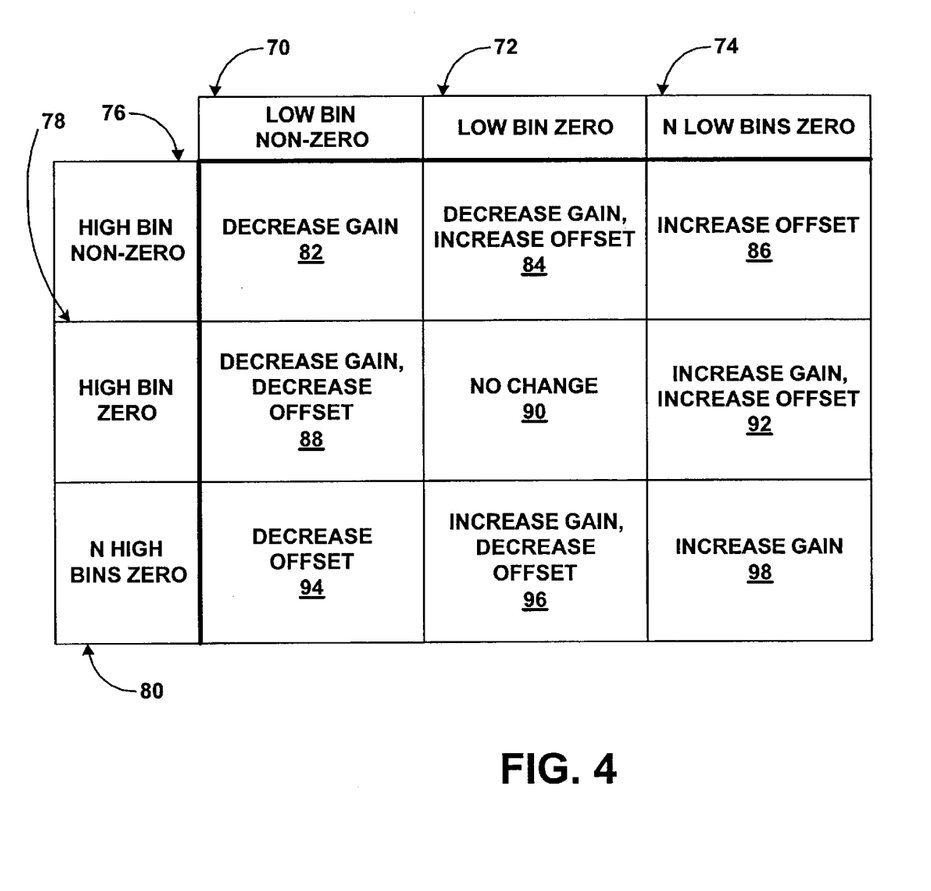
FIG. 4 is an exemplary decision matrix that illustrates the conditions that lead to adjustments of the mapping parameters.

FIG. 4 is an exemplary decision matrix that illustrates the example conditions that lead to adjustments of the mapping parameters, along with exemplary ways in which the adjustments may be made. Looking at the lowest bins, there are three possibilities. First, the bin holding the lowest value may hold a non-zero number (70). When the lowest bin is non-zero, there is a risk of data going out of range. Although it is not certain that the data in the histogram are out of range, or that data to be recorded in the new histogram will go out of range, there is a risk that data in the new histogram will go out of range unless an adjustment is made. Accordingly, microprocessor 36 makes an adjustment to the mapping parameters by adjusting the gain, the offset, or both of amplifier 32.

A second possibility is that there are N bins on the low end that are zero (74). N is a programmable integer representing a number of bins. When N is three, for example, microprocessor 36 checks the three lowest bins to determine whether those bins are empty. If the three lowest bins are empty, it is possible that there is range that is not being utilized. In other words, there is available room in the bins at the low end of the histogram. The presence of unused range suggests inefficient use of the range, and that there is room to enhance sensitivity. Accordingly, microprocessor 36 makes an adjustment to the gain, the offset, or both of amplifier 32, to utilize the unused range when generating the new histogram.

A third possibility is that the range on the low side of the histogram is good (72). The lowest bin is zero, so there is no indication that data are out of range. On the other hand, the N lowest bins are not all empty, indicating that low-end range is being used effectively. Microprocessor 36 may or may not adjust the gain and the offset of amplifier 32, based upon the contents of the highest bins.

Like the lowest bins, the highest bins have three possibilities. First, there may be a value in the highest bin (76), indicating the possibility that data are out of range. Second, the N highest bins may be unused (80), indicating that there is range that is not being utilized. Third, the range on the high side of the histogram is good (78). Depending on the contents of the high bins and the low bins, microprocessor 36 may make an adjustment to the gain, the offset, or both of amplifier 32.

When the low bin and the high bin are both non-zero (70, 76), then there is a risk of data going out of range on both the high and low end. Microprocessor 36 expands the range by decreasing the gain (82). In general, decreasing the gain maps the higher site pressures to lower binary values and the lower site pressures to higher binary values. As a result, a wider range of pressures can be mapped to the available binary values. In addition, each bin may store the number of digital values corresponding to a wider span of pressures. Decreasing the gain of amplifier 32 also results in a decrease in sensitivity.

In an illustrative example, a twenty-bin histogram stores the number of digital values corresponding to site pressures between 760 mm Hg and 860 mm Hg. Each bin corresponds to a span of five mm Hg. If both the highest and lowest bin include non-zero values, microprocessor 36 generates a control signal 42 that decreases the gain of amplifier 32. As a result, each bin in the subsequent histogram corresponds to a greater span, such as six mm Hg instead of five mm Hg. The decrease in gain decreases sensitivity to changes in pressure, but increases the range of pressures that can be stored in the histogram. With each bin in the subsequent histogram having a span of six mm Hg, for example, the new histogram can store the number of digital values corresponding to pressures between 750 mm Hg and 870 mm Hg.

When there is unused capacity on both ends of the histogram (74, 80), the opposite occurs. Microprocessor 36 shrinks the range by increasing the gain (98). As a result, each bin stores the number of digital values corresponding to a narrower pressure span.

In some circumstances, there may be a risk of data out of range at one end of the histogram, but unused capacity on the other end of the histogram. When there is unused capacity on the low end but a risk of out-of-range data on the high end (74, 76), microprocessor 36 generates a control signal 42 that increases the offset of amplifier 32 (86). That is, microprocessor 36 shifts the range toward the high end. There is little risk that the shift will cause data to go out of range on the low end, because at least three bins on the low end were not used when the previous histogram was generated.

In similar fashion, microprocessor 36 generates a control signal 42 to decrease the offset and move the range down (94) when there is unused capacity on the high end but there is a risk of out-of-range data on the low end (70, 80). Adjusting the offset need not involve adjusting the gain.

In another illustrative example, a histogram may store the number of digital values corresponding to site pressures between 760 mm Hg and 860 mm Hg. Microprocessor 36, upon checking the bins, finds that the lowest three bins are empty but that the highest bin is not. In response, microprocessor 36 may generate a control signal 42 to increase the offset (86) by, for example, ten mm Hg. In this way, the new histogram may store the number of digital values corresponding to pressures between 770 mm Hg and 870 mm Hg, and the distribution may be more centered in the histogram.

In some circumstances, the range on one side of the histogram is good (72, 78), but there may be a risk of out-of-range data at the other end of the histogram (70, 76), or there may be unused capacity on the other end of the histogram (74, 80). In those circumstances, microprocessor 36 generates a control signal 42 that adjusts the gain and the offset of amplifier 32 (84, 88, 92, 96) for the new histogram. When the range on both ends of the histogram is good (72, 78), however, no adjustment is needed (90).

The decision matrix shown in FIG. 4 is offered for purposes of illustration, and the invention is not limited to the particular matrix shown. In circumstances in which the range on one side of the histogram is good (72, 78), but range on the other side is not (70, 74, 76, 80), microprocessor 36 may, for example, generate a control signal 42 that adjusts only the gain of amplifier 32, without adjusting the offset in any way.

Microprocessor 36 uses techniques such as the decision matrix in FIG. 4 to determine whether an adjustment to the gain or offset or both should be made (56 in FIG. 3) and makes the adjustment accordingly (58). Microprocessor 36 records the adjustments in RAM 40 (60). The recorded gain and offset are useful for normalizing stored data (52), such as the mean, the standard deviation, or values at particular percentiles.

When the adjustments have been made and the mapping parameters have been recorded, the histogram data are reset (62). In other words, the distribution of data in the previous histogram may be discarded, and a new histogram may be generated (50). The new histogram is generated using the new mapping parameters.

Figure 5A:
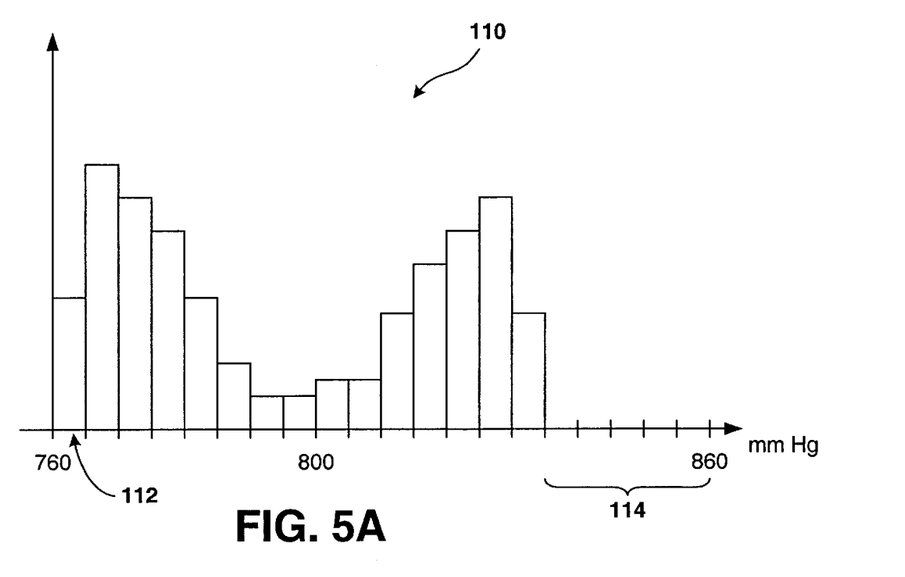
FIG. 5A is an exemplary histogram generated as a function of a set of mapping parameters.
Figure 5B:
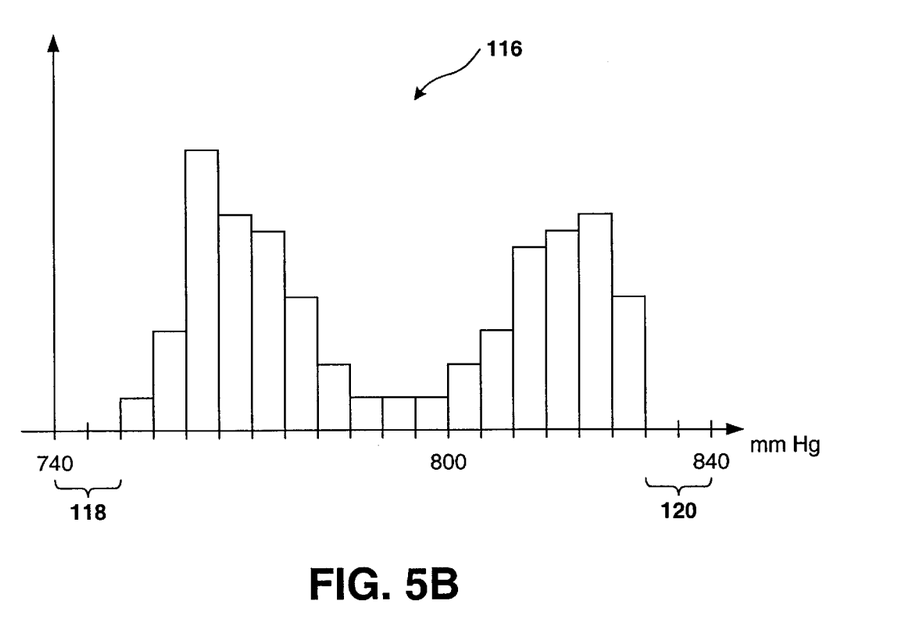
FIG. 5B is an exemplary histogram generated as a function of a set of adjusted mapping parameters, the mapping parameters adjusted as a function of the distribution in the histogram in FIG. 5A.

FIGS. 5A and 5B illustrate an example of the operation of the invention. Histogram 110 has been generated according to a distribution of site pressures sensed by pressure sensor 20. Histogram 110 has twenty bins, and records the distribution of binary values representing pressures between 760 mm Hg and 860 mm Hg. With these mapping parameters, site pressures below 760 mm Hg or above 860 mm Hg are out of range. An out-of-range site pressure will result in clipped digital pressure data.

The bin holding the lowest value 112 holds a non-zero number, indicating a risk of data out of range. Some data in lowest bin 112 may represent site pressures below 760 mm Hg, and these data may have been clipped. On the high end of the histogram, however, the five highest bins 114 are empty, indicating that high end range is not being utilized. The distribution of data in histogram 110, with the distribution disposed toward the low side, may be caused by the patient being in an environment in which the ambient pressure is low.

In response to the distribution of values in histogram 110, microprocessor 36 adjusts the offset of amplifier 32 upward, thereby mapping all site pressures to higher binary values. In the example shown in FIG. 5B, microprocessor 36 reduces the maximum and minimum pressures by 20 mm Hg, so that subsequent histogram 116 records a distribution of binary values representing site pressures between 740 mm Hg and 840 mm Hg. Microprocessor 36 does not change the gain.

Subsequent histogram 116, generated with the adjusted offset, produces the distribution shown in FIG. 5B. The distribution of subsequent histogram 116 is more centered than the distribution of previous histogram 110. The two lowest bins 118 and the two highest bins 120 are both empty, indicating that there is no risk of data out of range. Furthermore, the two unused bins on each end 118, 120 indicate acceptable utilization of the range. For the histogram that succeeds histogram 116, microprocessor 36 will keep the same mapping parameters, i.e., microprocessor 36 will not change the gain or the offset of amplifier 32.

The invention is capable of a number of advantages. Microprocessor 36 automatically corrects for risks of out-of-range data, due to changes in the ambient air pressure experienced by the patient. As a result, the risk of clipping data is reduced. In addition, it is unnecessary for the patient's physician to precisely set a fixed pressure range for implanted medical device 12. Consequently, the physician need not make estimations about factors that might affect the ambient pressure, such as the patient's altitude or travel habits.

Although microprocessor 36 automatically keeps the data in range, microprocessor 36 does so with little adverse effect on sensitivity. Furthermore, microprocessor 36 may increase sensitivity automatically when microprocessor 36 detects the presence of unused range. Microprocessor 36 automatically adjusts the mapping parameters so that range is used more efficiently, and in this way, microprocessor 36 maintains enhanced sensitivity.

Various embodiments of the invention have been described. These embodiments are illustrative of the practice of the invention. Various modifications may be made without departing from the scope of the claims. For example, the techniques described above adjust the gain and/or the offset of amplifier 32 while holding the number of histogram bins constant. The number of bins need not be constant.

The amount of gain adjustment made by microprocessor 36 may be a preselected amount. Alternatively, the amount of gain adjustment may be a function of the contents of the boundary bins. For example, the gain may be adjusted by a large magnitude when a boundary bin has a large number, and by a small magnitude when the boundary bin has a small number. Similarly, the offset adjustment may be a preselected amount or a function of the contents of the boundary bins. The invention encompasses all of these variations.

In addition, the invention may be embodied as a computer-readable medium comprising instructions that cause microprocessor 36 to carry out the techniques of the invention. The computer-readable medium includes physical media such as ROM 38, or a memory unit such as erasable programmable read-only memory, or magnetic or optical storage media. These and other embodiments are within the scope of the following claims.

What is claimed is:

1. A method comprising:
    mapping a set of blood pressures to a set of discrete binary values with first mapping parameters, wherein the first mapping parameters comprise a maximum binary value that corresponds to a maximum blood pressure and a minimum binary value that corresponds to a minimum blood pressure;
    generating a histogram with the set of discrete binary values where the histogram is compound of a plurality of bins; and
    generating second mapping parameters as a function of the contents of the lowest bin and the highest bin of the histogram.

2. The method of claim 1, further comprising:
    mapping a second set of blood pressures to a second set of discrete binary values with the second mapping parameters; and generating a second histogram with the second set of discrete binary values.

3. The method of claim 1, wherein generating the second set of mapping parameters comprises changing the gain of an amplifier.

4. The method of claim 3, wherein increasing the gain of the amplifier decreases the maximum blood pressure that corresponds to the maximum binary value and increases the minimum blood pressure that corresponds to the minimum binary value.

5. The method of claim 1, wherein generating the second mapping parameters comprises changing the offset of an amplifier.

6. The method of claim 5, wherein increasing the offset of the amplifier decreases the maximum blood pressure that corresponds to the maximum binary value and decreases the minimum blood pressure that corresponds to the minimum binary value.

7. The method of claim 1, wherein generating the second mapping parameters comprises corresponding the maximum binary value to a second maximum blood pressure.

8. The method of claim 1, wherein generating the second mapping parameters comprises corresponding the minimum binary value to a second minimum blood pressure.

9. The method of claim 1, further comprising generating the second mapping parameters as a function of the contents of the N lowest bins, N being an integer greater than one.

10. The method of claim 1, further comprising generating the second mapping parameters as a function of the contents of the N highest bins, N being an integer greater than one.

11. The method of claim 1, further comprising storing the second mapping parameters in memory.

12. A computer-readable medium comprising instructions for causing a programmable processor to:

map a set of blood pressures to a set of discrete binary values with a first set of mapping parameters, wherein the first set of mapping parameters comprises a maximum binary value that corresponds to a maximum blood pressure and a minimum binary value that corresponds to a minimum blood pressure;

generate a histogram with the set of discrete binary values where the histogram is compound of a plurality of bins; and generate a second mapping parameters as a function of the contents of the lowest bin and the highest bin of the histogram.

13. The medium of claim 12, the instructions further causing the programmable processor to:

map a second set of blood pressures to a second set of discrete binary values with the second mapping parameters; and generate a second histogram with the second set of discrete binary values.

14. The medium of claim 12, wherein generating the second mapping parameters comprises changing the gain of an amplifier.

15. The medium of claim 14, wherein increasing the gain of the amplifier decreases the maximum blood pressure that corresponds to the maximum binary value and increases the minimum blood pressure that corresponds to the minimum binary value.

16. The medium of claim 12, wherein generating the second mapping parameters comprises changing the offset of an amplifier.

17. The medium of claim 16, wherein increasing the offset of the amplifier decreases the maximum blood pressure that corresponds to the maximum binary value and decreases the minimum blood pressure that corresponds to the minimum binary value.

18. The medium of claim 12, wherein generating the second mapping parameters comprises corresponding the maximum binary value to a second maximum blood pressure.

19. The medium of claim 12, wherein generating the second mapping parameters comprises corresponding the minimum binary value to a second minimum blood pressure.

20. The medium of claim 12, the instructions further causing the programmable processor to generate the second mapping parameters as a function of the contents of the N lowest bins, N being an integer greater than one.

21. The medium of claim 12, the instructions further causing the programmable processor to generate the second mapping parameters as a function of the contents of the N highest bins, N being an integer greater than one.

22. The medium of claim 12, the instructions further causing the programmable processor to store the second mapping parameters in memory.

23. A device comprising:

an amplifier that generates pressure signals as a function of pressure sensed by a pressure sensor in a body, the amplifier responsive to mapping parameters;

an analog-to-digital converter that converts the pressure signals to a set of discrete binary values; and a controller that generates a first histogram as a function of a distribution of a first set of binary values and first mapping parameters and that generates second mapping parameters as a function of the distribution of data in the first histogram.

24. The device of claim 23, wherein the controller generates a second histogram as a function of the distribution of a second set of binary values and the second mapping parameters.

25. The device of claim 23, further comprising the pressure sensor.

26. The device of claim 23, further comprising memory that stores the first mapping parameters and the second mapping parameters.

27. The device of claim 23, wherein the controller controls the mapping parameters and wherein controlling the mapping parameters includes adjusting the gain of the amplifier.

28. The device of claim 27, wherein the first mapping parameters comprise a maximum binary value that corresponds to a maximum pressure and a minimum binary value that corresponds to a minimum pressure, and wherein increasing the gain of the amplifier decreases the maximum pressure that corresponds to the maximum binary value and increases the minimum pressure that corresponds to the minimum binary value.

29. The device of claim 23, wherein the controller controls the mapping parameters and wherein controlling the mapping parameters includes adjusting the offset of the amplifier.

30. The device of claim 29, wherein the first mapping parameters comprise a maximum binary value that corresponds to a maximum pressure and a minimum binary value that corresponds to a minimum pressure, and wherein increasing the offset of the amplifier decreases the maximum pressure that corresponds to the maximum binary value and decreases the minimum pressure that corresponds to the minimum binary value.

31. The device of claim 23, wherein the controller generates the second mapping parameters by changing the first mapping parameters as a function of the contents of the lowest bin and the highest bin of the first histogram.

32. A method comprising:

receiving analog pressure data;

mapping the analog pressure data to discrete binary values with first mapping parameters;

generating a first histogram as a function of the distribution of the discrete binary values during a storage interval where the histogram is compound of a plurality of bins; and after the storage interval, generating second mapping parameters as a function of the contents of the lowest bin and the highest bin of the histogram.

33. The method of claim 32, further comprising storing the second mapping parameters.

34. The method of claim 32, wherein generating the second mapping parameters comprises changing the gain of an amplifier.

35. The method of claim 32, wherein generating the second mapping parameters comprises changing the offset of an amplifier.

36. The method of claim 32, further comprising generating the second mapping parameters as a function of the contents of the N lowest bins, N being an integer greater than one.

37. The method of claim 32, further comprising generating the second mapping parameters as a function of the contents of the N highest bins, N being an integer greater than one.

38. The method of claim 32, wherein generating the second mapping parameters comprises adjusting the first mapping parameters.

\* \* \* \* \*